US00PP13192P2

(12) United States Plant Patent
Utecht

(10) Patent No.: US PP13,192 P2
(45) Date of Patent: Nov. 5, 2002

(54) GERANIUM PLANT NAMED 'FISROYAL'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/991,636

(22) Filed: Nov. 26, 2001

(65) Prior Publication Data

US 2002/0083504 P1 Jun. 27, 2002

(51) Int. Cl.[7] ..... A01H 5/00

(52) U.S. Cl. ..... Plt./329

(58) Field of Search ..... Plt./329

*Primary Examiner*—Kent L. Bell
(74) *Attorney, Agent, or Firm*—Foley & Lardner

(57) ABSTRACT

A new and distinct cultivar of geranium plant named 'Fisroyal', as described and illustrated, and particularly characterized by the combined features of deep cherry-red, round, semi-double flowers with small, dark-red markings, medium green foliage with slight zonation, and medium to tall, but low, rounded foliage canopy.

1 Drawing Sheet

BOTANICAL CLASSIFICATION

*Pelargonium zonale.*

VARIETY DENOMINATION

'Fisroyal'.

BACKGROUND OF THE INVENTION

The present invention comprises a new and distinct cultivar of geranium, botanically known as *Pelargonium zonale*, and hereinafter referred to by the cultivar name 'Fisroyal'.

'Fisroyal' is a product of a planned breeding program which had the objective of creating new geranium varieties with magenta to purple flower color, medium green foliage in combination with medium to tall plant habit.

'Fisroyal' originated from a hybridization made by the inventor Angelika Utecht in a controlled breeding program in Galdar, Gran Canaria, Spain, in 1996. The female parent was a hybrid seedling, no. K94-1960-1, having purple-pink, single-type flowers, large inflorescences, dark-green foliage, with only very weak zonation, and medium sized, but somewhat open and irregular plant habit. The male parent of 'Fisroyal' was the patented variety 'HWD Violetta' (U.S. Plant Pat. No. 9,748), characterized by red-purple, semi-double flowers, medium green foliage with slight zonation, and medium sized plant habit.

'Fisroyal' was selected as one flowering plant within the progeny of the stated cross by Angelika Utecht in 1997, in a controlled environment in Galdar, Gran Canaria, Spain. The first act of asexual reproduction of 'Fisroyal' was accomplished when vegetative cuttings were taken from the initial selection in the fall of 1997, in a controlled environment in Galdar, Gran Canaria, Spain, by, or under the supervision of, Angelika Utecht.

Horticultural examination of plants grown from cuttings of the plant initiated in May 1998, in Hillscheid, Federal Republic of Germany, and continuing thereafter, has demonstrated that the combination of characteristics as herein disclosed for 'Fisroyal' are firmly fixed and are retained through successive generations of asexual reproduction. The new cultivar reproduces true to type.

'Fisroyal' has not been observed under all possible environmental conditions. The phenotype may vary significantly with variations in environment such as temperature, light intensity and day length. The following observations, measurements, and comparisons describe plants grown in Hillscheid, Germany, and in Langley, British Columbia, Canada, under greenhouse conditions which approximate those generally used in commercial practice.

BRIEF DESCRIPTION OF THE INVENTION

The following traits have been repeatedly observed and are determined to be basic characteristics of 'Fisroyal' in combination distinguish this geranium as a new and distinct cultivar:

1. Round, deep cherry-red colored flowers;

2. Medium sized, semi-spherically shaped umbels borne well above the foliage;

3. Medium green foliage with slight zonation on young leaves;

4. Moderately vigorous growth, medium to tall, lowly mounded plant habit, and

5. Early to medium season spring flowering response.

Of the many commercial cultivars known to the present inventor, the most similar in comparison to 'Fisroyal' is the variety 'Fispurple' (U.S. Plant Pat. No. 12,368), the parental cultivar 'HWD Violetta' and the related, cultivar 'Fisromag' (U.S. Plant patent application Ser. No. 09/991,976).

In comparison to 'Fispurple', 'Fisroyal' has similarly shaped flowers and umbels, but the flower color is a less bluish hue, and unlike with 'Fispurple', there are small, deep-red macules. Furthermore, 'Fisroyal' grows somewhat more vigorously than 'Fispurple'.

In comparison to 'HWD Violetta', 'Fisroyal' has a deeper red, less bluish hue of flower color, small markings on petals, in contrast to 'HWD Violetta', and weaker zonation on leaves.

In comparison to 'Fisromag', the flower color of 'Fisroyal' is a more reddish, less bluish hue, and 'Fisroyal' grows somewhat more vigorously.

BRIEF DESCRIPTION OF THE DRAWING

The accompanying photographic drawing shows typical flower and foliage characteristics of 'Fisroyal' with colors being as true as possible with an illustration of this type.

The drawing shows a flowering pot plant in a 14 cm container.

DETAILED BOTANICAL DESCRIPTION

In the following description color references are made to The Royal Horticultural Society Colour Chart. The color values were determined indoors from flowering plants growing in a green-house in May 2001 in Hillscheid, Germany. The measurements were taken in Langley, British Columbia, Canada in early July 2001, 18 weeks after planting of rooted cuttings. The plants were growing in 8 inch containers and had not been pinched.

Inflorescence:
- *Type.*—Umbel.
- *Shape.*—Semi-spherical.
- *Average diameter.*—107 mm.
- *Average depth.*—59 mm.
- *Peduncle length.*—192 mm.
- *Peduncle color.*—Light green, RHS 144 A, outdoors reddish infused with RHS 179 B.
- *Pedicel length.*—26 mm.
- *Pedicel color.*—Light green, RHS 144 B, upper part reddish, RHS 184 A.
- *Number of flowers per umbel.*—About 25–30.

Corolla:
- *Average diameter.*—46 mm.
- *Form.*—Semi-double.
- *Shape.*—Round, cup-shaped.
- *Number of petals.*—Average 9.1.
- *Number of petaloids.*—1–2, narrow, same color as the petals.
- *Shape of petals.*—Obovate, base attenuate, upper end is rounded, margin is entire.
- *Size of petals.*—Upper petals: length 26–28 mm; width 20–22 mm. Lower petals: length 25–26 mm; width 23–25 mm.
- *Color (general tonality from a distance of three meters).*—Deep cherry-red.
- *Color of upper petals.*—Slightly more reddish hue than RHS 57 A.
- *Markings of upper petals.*—Red macule, RHS 45 A, about 5 mm in diameter in the middle of the petal, and salmon-red base, RHS 43 B.
- *Color of lower petals.*—Slightly more reddish than RHS 57 A.
- *Markings of lower petals.*—Small, about 3 mm in diameter, deep red colored macules, between RHS 46 A and RHS 46 B.
- *Color of lower surface of petals.*—Upper petals RHS 45 C., lower petals RHS 53 D.
- *Color of sepals.*—Outer surface light green, RHS 144 A, base brown, RHS 179 A, inner surface light green, RHS 144 B, base RHS 179 B.
- *Number of sepals.*—5.
- *Shape of sepals.*—*Linear to lanceolate, acute tip, truncate base, surface with very short pubescence, margin entire.*
- *Size of sepals.*—10–11 mm long, 4 mm wide for the largest upper sepal, 3 mm for the other sepals.

Bud (just before petals unfold):
- *Shape.*—Elliptical to round.
- *Color (sepals).*—Green, RHS 144 A.
- *Color (petals).*—RHS 57 B.
- *Length.*—15 mm.
- *Width.*—10 mm.

Reproductive organs:
- *Androecium.*—About 5 fertile anthers, filaments white, RHS 155 moderate pollen, orange, RHS 30A.
- *Gynoecium.*—One pistil, style and stigma dull red, RHS 53 B, 5 to 6 lobed stigma.
- *Fertility/seed set.*—Occasionally a few seeds are developed. Fruit: Oblong, about 5–6 mm in diameter, with rostrum (beak), total length about 40 mm. Seed: Oblong, 4–5 mm long, brown, RHS 177 B.

Spring flowering response period: In Hillscheid, Germany, in 2000 plants had on average 1.1 flowers opened 8 weeks after planting of rooted cuttings.

Outdoor flower production: Continuously flowering, the flower count in 2000 in Hillscheid, Germany, indicated on average 2.0 inflorescence per plant in mid May.

Durability: Good stability of flower color, very little fading relatively good rain resistance.

Lastingness of the individual flower: About 8–9 days at 18° C., about 18 days for the umbel.

Pest/disease resistance/susceptibility: No observations to date.

Fragrance: None.

PLANT

Foliage:
- *Shape.*—Kidney-shaped, with open, cordate base, and weak lobes.
- *Margin.*—Bicrenated, somewhat wavy.
- *Texture.*—Upper surface smooth, velvety.
- *Size of leaf.*—87.5 mm wide, 56.5 mm long.
- *Color of upper surface.*—Medium green, approximately RHS 137 B to RHS 137 C.
- *Color of zonation.*—Very weak, darker green, about RHS 147 A, zonation may not be visible on mature leaves during the summer.
- *Color of lower surface.*—RHS 137 D.
- *Petioles.*—45–55 mm long, 3.0 mm diameter, light green in color, approximately RHS 143 C.

General appearance and form:
- *Stem color.*—Light green, RHS 143 C to RHS 144 D.
- *Internode length.*—10–15 mm.
- *Branching pattern.*—8.0 branches.
- *Size of plants.*—Height 29.6 cm, width 49.6 cm, as measured from the top of the soil (base of the main stem) to the surface of the foliage canopy measured without inflorecences.

I claim:

1. A new and distinct cultivar of geranium plant named 'Fisroyal', as described and illustrated herein.

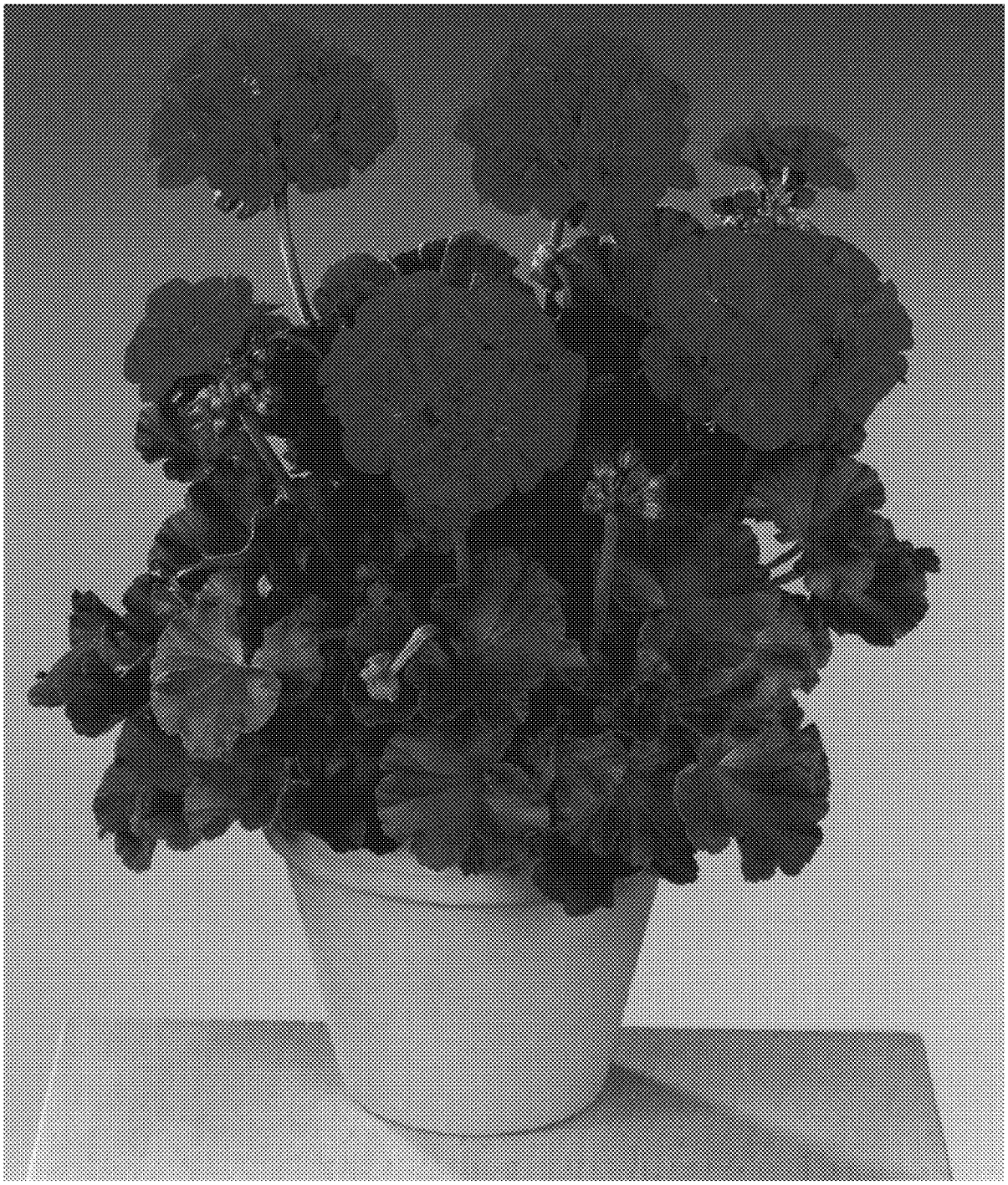

* * * * *